United States Patent
Kreβner

(10) Patent No.: US 8,474,085 B2
(45) Date of Patent: Jul. 2, 2013

(54) TOOTHBRUSH AND ATTACHMENT THEREFOR

(75) Inventor: Gerhard Kreβner, Altenstadt (DE)

(73) Assignee: Braun GmbH, Kronberg (DE)

( * ) Notice: Subject to any disclaimer, the term of this patent is extended or adjusted under 35 U.S.C. 154(b) by 829 days.

(21) Appl. No.: 12/519,508

(22) PCT Filed: Dec. 7, 2007

(86) PCT No.: PCT/EP2007/010672
§ 371 (c)(1),
(2), (4) Date: Jan. 26, 2010

(87) PCT Pub. No.: WO2008/074410
PCT Pub. Date: Jun. 26, 2008

(65) Prior Publication Data
US 2010/0162498 A1    Jul. 1, 2010

(30) Foreign Application Priority Data
Dec. 18, 2006   (DE) .................. 10 2006 060 134

(51) Int. Cl.
*A61C 17/22*    (2006.01)

(52) U.S. Cl.
USPC ......... 15/22.1; 15/176.1; 403/109.5; 403/110

(58) Field of Classification Search
USPC ............... 15/22.1, 22.2, 23, 28, 176.1, 176.6; 403/109.5, 110, 195, 202, 240, 292–293, 403/300, 313, 314
See application file for complete search history.

(56) References Cited

U.S. PATENT DOCUMENTS

| | | | |
|---|---|---|---|
| 3,851,984 A * | 12/1974 | Crippa | 403/322.4 |
| 3,927,435 A * | 12/1975 | Moret et al. | 15/176.1 |
| 5,289,604 A | 3/1994 | Kressner | |
| 5,365,627 A | 11/1994 | Jousson et al. | |
| 6,367,108 B1 | 4/2002 | Fritsch et al. | |
| 2003/0135940 A1 | 7/2003 | Lev et al. | |
| 2004/0255409 A1 | 12/2004 | Hilscher et al. | |
| 2005/0108838 A1 * | 5/2005 | Schaefer et al. | 15/22.1 |

FOREIGN PATENT DOCUMENTS

| | | | |
|---|---|---|---|
| DE | 24 30 921 | | 1/1976 |
| DE | 4234764 | * | 4/1994 |
| DE | 195 48 086 | | 8/1996 |
| DE | 297 02 508 | | 6/1998 |
| DE | 103 52 993 | | 6/2005 |
| EP | 585738 | | 3/1994 |
| EP | 0 500 537 | | 11/1994 |
| JP | 5-146314 | * | 6/1993 |
| JP | 05-146314 | | 6/1993 |
| JP | 5-207914 | * | 8/1993 |

(Continued)

*Primary Examiner* — Mark Spisich
(74) *Attorney, Agent, or Firm* — John P. Colbert; Vladimir Vitenberg

(57) ABSTRACT

An electric toothbrush includes a handpiece and a mountable attachment. The attachment includes a working head and a coupling member which is joined to the working head and connectable to the toothbrush handpiece by positive and/or frictional engagement. The attachment can be an attachment brush for dental cleansing, or for interproximal cleaning devices, such as gum massage heads or other attachment tools for performing similar tasks in the oral cavity. The coupling member is braced against the toothbrush handpiece, to provide a low to zero-play connection which accommodates production tolerances. At least one pivot lever or toggle joint is provided for clamping the coupling member upon the toothbrush handpiece.

24 Claims, 3 Drawing Sheets

FOREIGN PATENT DOCUMENTS

| | | | |
|---|---|---|---|
| JP | 05-207914 | | 8/1993 |
| JP | 585738 | * | 3/1994 |
| JP | 8-224259 | * | 9/1996 |
| JP | 08-224259 | | 9/1996 |
| JP | 08-299372 | | 11/1996 |
| JP | 8-299372 | * | 11/1996 |
| JP | 10-023928 | | 1/1998 |
| JP | 10-23928 | * | 1/1998 |
| JP | 11-235234 | * | 8/1999 |
| JP | 2001-524331 | | 12/2001 |
| JP | 2002-113024 | * | 4/2002 |

* cited by examiner

B-B

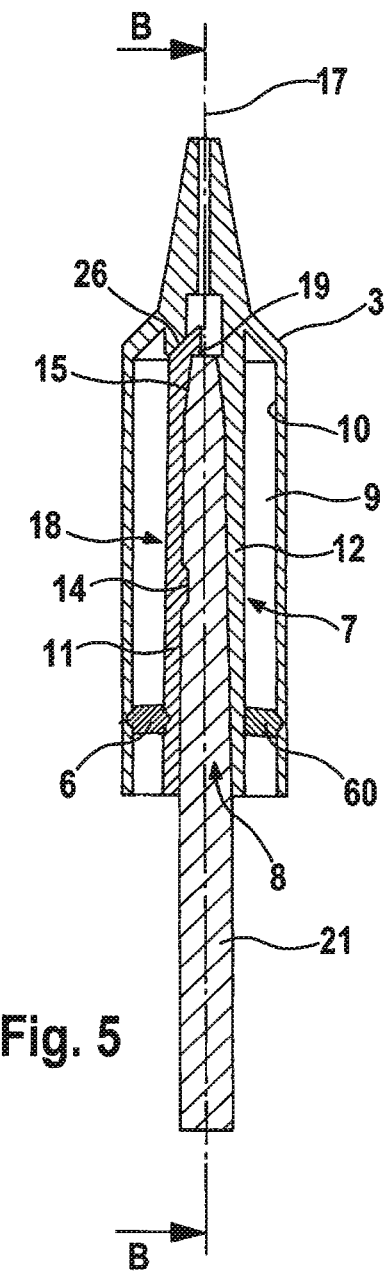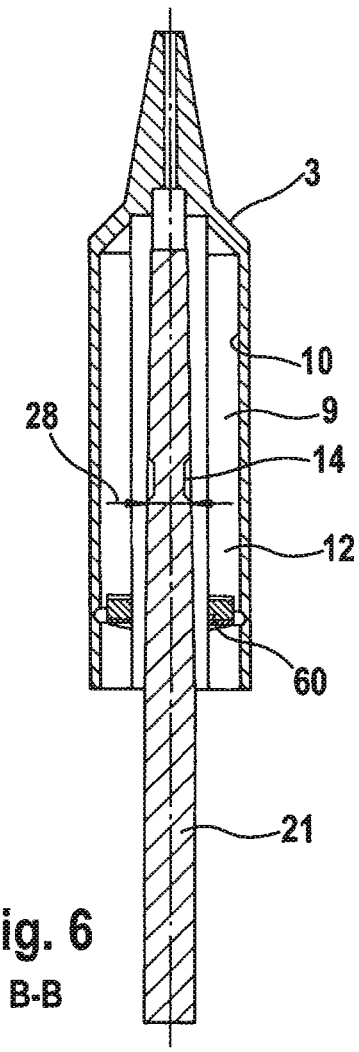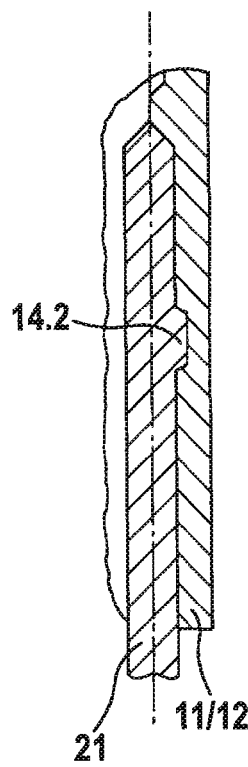
Fig. 5  Fig. 6 B-B  Fig. 7

TOOTHBRUSH AND ATTACHMENT THEREFOR

BACKGROUND

This invention relates generally to an electric toothbrush having a handpiece and a mountable working head attachment and in particular, to a coupling member which is joined to the working head and connectable to the toothbrush handpiece. Powered oral care attachments can include attachment brushes for dental cleansing, as well as interproximal cleaning devices, such as gum massage heads or other attachment tools for performing similar tasks in the oral cavity.

Various toothbrush attachments and connection means have been proposed, providing, in some cases, attachments with excess slack in the connections or with excessively tight tolerances. Accordingly, improvements are sought in toothbrush attachments and toothbrush attachment connections.

SUMMARY

The details of one or more embodiments of the invention are set forth in the accompanying drawings and the description below. Other features, objects, and advantages of the invention will be apparent from the description and drawings, and from the claims.

One aspect of the invention features an attachment for an electric toothbrush, including a working head; a coupling member joined to the working head, and detachably connectable to a toothbrush handpiece by at least one of positive engagement and frictional engagement; and at least one pivot lever configured to clamp the coupling member upon the toothbrush handpiece.

In some cases the coupling member includes a mount into which a connecting member of the toothbrush handpiece is insertable, with the lever being provided for securely clamping the mount against the connecting member. In particular cases, the mount is conically shaped or forms one of a longitudinally slotted sleeve and a multi-part sleeve.

In some implementations, the coupling member includes an inner recess into which the connecting member of the toothbrush handpiece is insertable, with the lever being arranged in the inner recess and adapted to be braced between an inner contour of the inner recess and the connecting member of the toothbrush handpiece.

In a particular implementation, the coupling member includes a mounting member which is shaped to conform to the connecting member of the toothbrush handpiece, radially and axially movably mounted in relation to a longitudinal axis of the coupling member and is adapted to be moved by the lever onto the connecting member of the toothbrush handpiece. In some cases, the coupling member includes an inner recess into which the connecting member of the toothbrush handpiece is insertable, with the lever being arranged in the inner recess and adapted to be braced between an inner contour of the inner recess and the connecting member of the toothbrush handpiece; and wherein the mounting member is arranged in the inner recess of the coupling member and spaced from the inner contour of the inner recess, with the lever being arranged between the inner contour of the inner recess and the mounting member.

In some instances the mounting member forms a preferably half-shell-shaped mounting shell having a contour shaped to closely conform to the connecting member of the toothbrush handpiece in coupled condition. In a particular implementation, the coupling member includes a mount into which a connecting member of the toothbrush handpiece is insertable, with the lever being provided for clamping the mount against the connecting member, and the mounting member forms at least part of the mount.

In some cases, the mounting member includes at least one flattening.

In a particular implementation, the lever is configured to be self-actuating so that when the attachment is plugged onto the toothbrush handpiece, the lever pivots into its clamping position, and pivots into a released position when the attachment is pulled off the toothbrush handpiece.

In some cases, the lever is overstraightened when in its clamping position.

In a particular implementation, the coupling member is connectable to the toothbrush handpiece using an axial movement along a longitudinal axis of the coupling member, and the lever is pivotal about a transverse axis transverse to the longitudinal axis. In some cases, a lever actuator is provided that is axially movable relative to the coupling member longitudinal direction, the actuator including a follower element that engages the toothbrush handpiece on plugging the attachment onto the toothbrush handpiece, and being operatively associated with the lever by connecting means in such a way that, on plugging on the attachment, the lever actuator becomes displaced axially, thereby moving the lever into its clamping position. In some cases the lever actuator is formed by the mounting member, which is shaped to conform to the connecting member of the toothbrush handpiece. In some cases, the connection is configured for positive engagement, and/or include a mounting recess and a projection engaging therein.

In a particular implementation, the lever is of a half-ring-shaped configuration.

In a particular implementation, a pair of opposite levers is provided forming a toggle joint. In some cases the toggle joint forms one of a slotted ring and a ring split into two pivoted segments into which the connecting member of the toothbrush handpiece is insertable. In some cases the coupling member includes a mount into which a connecting member of the toothbrush handpiece is insertable, with the lever being provided for clamping the mount against the connecting member, and the ring embracing the mount.

In some cases, the lever is pivotally mounted on a pivot formed with the coupling member.

In some cases, the coupling member is shaped to conform to a drive shaft of the toothbrush handpiece, and is adapted to be clamped upon the drive shaft by means of the lever.

Another aspect of the invention features a toothbrush including a toothbrush handpiece; and an attachment. The attachment includes a working head; a coupling member joined to the working head, and detachably connectable to a toothbrush handpiece; and at least one pivot lever configured to clamp the coupling member upon the toothbrush handpiece.

In some cases, the toothbrush handpiece includes one of a cylindrical and a conically tapered drive shaft.

In some cases, the drive shaft includes one of a flattening and a projection.

In some cases, the attachment is connectable via the drive shaft.

Another aspect of the invention features a coupling member firmly braced with the toothbrush handpiece in order to obtain a low to zero-play or low slack connection which accommodates a desired range of tolerances. In a particular implementation, at least one pivot lever is provided for clamping the coupling member to the toothbrush handpiece. It is advantageous in some cases for two pivot levers to combine to form a device referred to as a toggle joint. By using a toggle joint, greater actuating forces can be produced in the longitudinal direction of the leg by the application of a lesser amount of force on the leg forming the toggle joint, enabling the attachment to be firmly clamped in place even when a lesser amount of force is used for seating the attachment onto the toothbrush handpiece.

An additional feature of a toggle joint, which enables a firm and low to zero-play or low slack connection to be accomplished between the attachment and the toothbrush handpiece, includes allowance for normal manufacturing tolerances, with a cylindrical or conical fit between the attachment and the toothbrush handpiece. The coupling member of the attachment includes a conical mount into which complementary conical connecting member of the toothbrush handpiece is insertable creating a close, snug, or tight fit. The toggle joint clamps the conical mount against the conical counterpart of the toothbrush handpiece. The counterpart can be formed generally by different sections of the toothbrush handpiece, for example, the attachment can be firmly clamped upon a shank section which projects from the front end of the handpiece.

In one implementation, the attachment can be firmly clamped upon a drive shaft extending from the front end of the toothbrush handpiece. In this implementation, the conical mount can be shaped to conform to the complementary conical drive shaft, so that the toggle joint firmly clamps the mount of the coupling member onto the drive shaft of the toothbrush handpiece.

In a particular implementation, the conical fit between the attachment and the toothbrush handpiece is self-clamping. This can be accomplished by providing the conical surfaces with a bevel of less than 7 degrees. By virtue of the self-clamping configuration of the conical mount and the corresponding mating contour on the toothbrush handpiece, the attachment can be securely held on the toothbrush handpiece even without the aid of the toggle joint. The toggle joint, however, ensures a firmer low to zero-play or low slack connection in the presence of dimensional and shape tolerances and enhances the self-locking effect.

The connecting member of the toothbrush handpiece is insertable into the mount of the coupling member. In a particular implementation, the drive shaft inserts into a sleeve, which can be a longitudinally slotted and/or multi-part sleeve. The sleeve is arranged in the coupling member by positive or frictional engagement and can surround the drive shaft of the toothbrush handpiece. If the sleeve is made up of a plurality of parts which surround the drive shaft from opposite sides, at least one part of the sleeve can be integrally formed with the coupling member.

In a particular implementation, the toggle joint is formed integral with the coupling member. In some cases the toggle joint is arranged in an inner recess in the coupling member into which the connecting member of the toothbrush handpiece is insertable, with the toggle joint adapted to be braced between an inner contour of the inner recess and the connecting member of the toothbrush handpiece.

It is possible for the toggle joint to be seated directly on the connecting member of the toothbrush handpiece or to act on it so that the connecting member on the handpiece is braced against the attachment inner contour lying opposite the toggle joint. In one implementation, the toggle joint braces a mounting member against the connecting member of the toothbrush handpiece. In this implementation, the mounting member can be shaped to conform to the connecting member of the toothbrush handpiece and, related to a longitudinal axis of the coupling member, can be radially movably mounted in the inner recess of the coupling member of the attachment. The toggle joint can be located between the mounting member and an inner contour of the coupling member embracing the mounting member, so that the toggle joint, in taking support on the outer lying inner contour of the coupling member, can brace the mounting member against the inserted connecting member of the toothbrush handpiece.

In this implementation, the mounting member can form at least part of the aforementioned sleeve-shaped mount which is arranged in the interior of the coupling member of the attachment. In a particular implementation, the mounting member can form a half-shell-shaped mounting shell that fits around the connecting member of the toothbrush handpiece when coupled. The two half-shell-shaped mounting shells can combine to form the aforementioned sleeve-shaped mount into which the drive shaft of the toothbrush handpiece is fittingly received.

In some implementations, the mounting member and the connecting member of the toothbrush handpiece can have a uniformly arched contour as seen in cross-section. In a particular implementation, both the mounting member and the connecting member of the toothbrush handpiece include at least one flattening so that both frictional engagement and positive engagement are achieved between the coupling member and the connecting member on the handpiece. Not only does this provide for a better safeguard of the attachment against rotation about the toothbrush longitudinal axis, but it also enables an improved axial securing of the attachment, especially in the presence of a limited axial length of the flattened surface.

For ease of operation of the toothbrush, the toggle joint can be configured to be self-actuating, so that when the attachment is plugged onto the toothbrush handpiece, the toggle joint pivots automatically into its clamping position. The toggle joint also pivots automatically into its released position when the attachment is pulled off the handpiece of the toothbrush. Accordingly, the pivoting movement of the toggle joint, during the plugging-on movement of the attachment onto the toothbrush handpiece, obviates the need to provide for separate actuation of the toggle joint.

Depending on the configuration of the coupling member, various attaching movements can be considered. In some implementations, it is possible to combine a plug-on movement with a rotary movement. In a particular implementation, the attachment can be connected to the toothbrush handpiece using an axial movement along the coupling member longitudinal axis or along the toothbrush longitudinal axis. With such a configuration, the toggle joint can pivot about an axis transverse to the coupling member longitudinal axis. This enables the attaching movement to pivot the toggle joint automatically into its clamping position as the attachment is being seated onto the toothbrush handpiece, and to pivot it into its released position during detachment.

In this implementation, the toggle joint can be entrained or received directly by the connecting member of the toothbrush handpiece to be clamped, for example by the drive shaft, and be urged into its clamping position. In one implementation, a follower tab can be provided on the connecting member of the toothbrush handpiece to be inserted into the coupling member of the attachment. The tab then exerts pressure on the toggle joint and forces it into its clamping position as the toothbrush handpiece is plugged into the attachment.

In another implementation, a separate lever actuator can be used to actuate the lever or toggle joint. The actuator includes a follower element that engages the toothbrush handpiece upon plugging on the attachment. The actuator is also operatively associated with the toggle joint in such a way that upon plugging on the attachment, the separate lever actuator becomes displaced axially relative to the coupling member of the attachment, thereby moving the toggle joint into its clamping position. In a particular implementation, the lever actuator can be formed by the mounting member, shaped to conform to the handpiece connecting member, such as the drive shaft. For this purpose, the mounting member can be arranged for axial displacement in the inner recess of the coupling member of the attachment. When the mounting member engages the drive shaft of the handpiece, the mounting member moves deeper into the attachment as the plug-on movement continues. Because of the connection between the mounting member and the toggle joint, the toggle joint is pivoted, causing the mounting member to be urged into engagement with the drive shaft with increased force. Conversely, when the attachment is pulled off, the drive shaft of the handpiece, which is pulled out in the process, initially entrains or receives the axially movable mounting member, whereby the toggle joint is released, causing the locking engagement between the coupling member and the drive shaft to be reduced or released, so that the drive shaft can be withdrawn.

In a particular implementation, the toggle joint is approximately half-ring-shaped, forming a conformably shaped spacer between the half-shell-shaped mounting member, which it braces, and the inner contour of the section of the attachment embracing the mounting member.

While a single lever can generally suffice for clamping, a plurality of levers can be provided, lying opposite one another in pairs forming a toggle joint. In a particular implementation, two levers combine to form a slotted ring into which the connecting member of the toothbrush handpiece is insertable. The slotted ring surrounds the mounting sleeve, which is braced against the drive shaft of the toothbrush handpiece by the actuating forces of the levers. It is also possible to provide a plurality of toggle joints.

In a particular implementation, the levers are pivotally mounted on a pivot formed with the coupling member. Where two substantially half-ring-shaped levers are provided in relative opposite arrangement, they can be formed as separate parts. In another implementation, they can be connected to each other along a line of desired bending such that the resulting toggle joint ring comprises two half-ring-shaped lever sections that are tiltable towards each other. The toggle joint is then formed by pivotally connected ring segments of a ring integrally made of one piece.

Thus the attachment brush can be directly fastened to the drive shaft of the handpiece a low to zero-play connection which accommodates production tolerances. This can further serve to avoid angular losses which may occur as a result of the acceleration of the attachment brush by the drive shaft. The movements generated by the handpiece are thus more directly transmitted to the attachment brush.

The details of one or more implementations or embodiments of the invention are set forth in the accompanying drawings and description below. Other features, objects, and advantages of the invention will be apparent from the description and drawings, and from the claims.

DESCRIPTION OF DRAWINGS

Like reference symbols in the various drawings indicate like elements.

FIG. 5 is a longitudinal sectional view of one implementation of the coupling region between the attachment brush and the drive shaft of the toothbrush in which the drive shaft includes a flattening and the mounting member embracing it includes a projection.

FIG. 6 is a longitudinal sectional view of the coupling region of the embodiment of FIG. 5, which is turned through 90° compared to the longitudinal section of FIG. 5.

FIG. 7 is a part sectional view of the coupling region illustrating one variant of the embodiment of FIG. 5 or 6, in which the drive shaft includes a projection and the mounting member embracing it includes a flattening.

DETAILED DESCRIPTION

Figure 1:
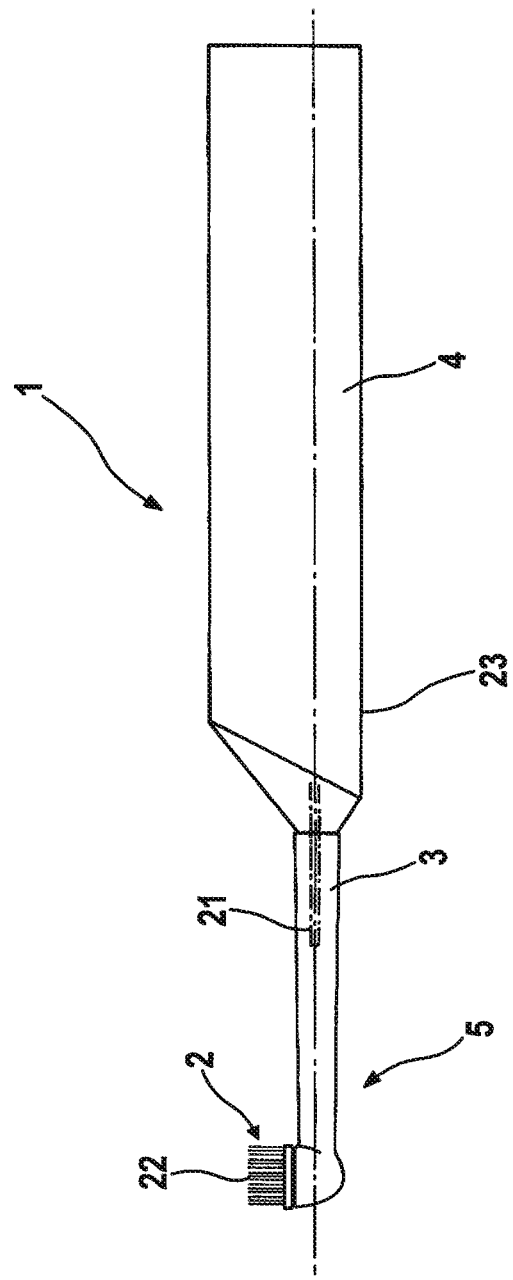
FIG. 1 is a schematic side view of one implementation of an electric toothbrush having a handpiece and an attachment brush which is directly attached to a drive shaft projecting from the handpiece.

The toothbrush 1 shown in FIG. 1 comprises a handpiece 4 which forms a handle and supports a replaceable attachment in the form of an attachment brush 5. The attachment brush 5 comprises a working head 2 with a set of bristles 22, which is connected by a coupling member 3 in the form of a brush tube to the handpiece 4. In this arrangement, the attachment brush 5 is seated on a drive shaft 21 protruding from the front end of the housing 23 of the handpiece 4 and forming a connecting member 8 (FIG. 2) of the handpiece for the attachment brush 5. The drive shaft 21 can perform various drive movements, for example, an oscillatory rotational movement and/or a translational drive movement for driving the working head 2 of the attachment brush 5. The drive shaft 21 is driven by an electric drive provided in the handpiece 4, which is not shown separately.

Figure 3:
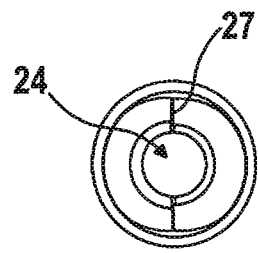
FIG. 3 is an end view one implementation of the coupling region between the attachment brush and the drive shaft of the handpiece, showing the configuration of the levers for clampingly holding the drive shaft.
Figure 2:
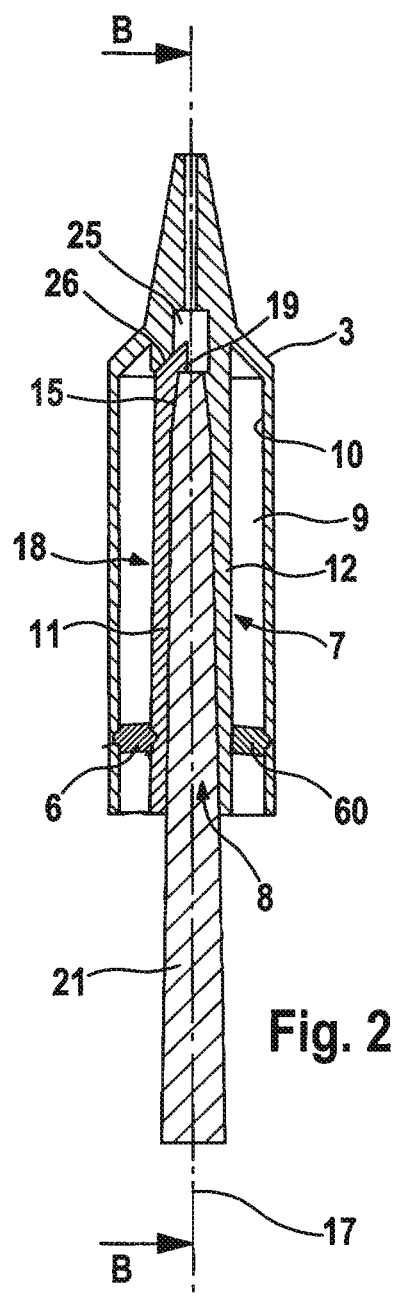
FIG. 2 is a fragment of a longitudinal sectional view of one implementation of the toothbrush of FIG. 1, showing the coupling region between the attachment brush and the drive shaft of the handpiece.
Figure 4:
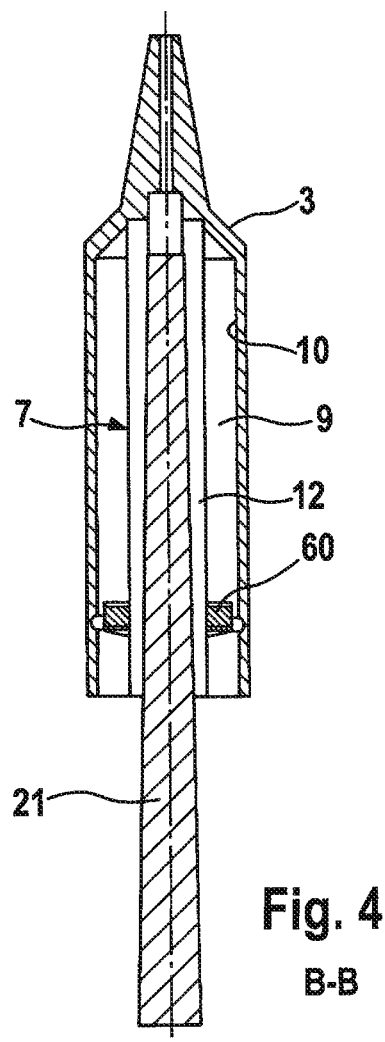
FIG. 4 is a longitudinal sectional view of one implementation of the coupling region between the attachment brush and the drive shaft, which is turned through 90° compared to the illustration in FIG. 2.

FIGS. 2 through 4 show the releasable connection between the attachment brush 5 and the handpiece 4 in greater detail. The coupling member 3 of the attachment brush 5 includes a substantially cylindrical inner recess 9, which, in the manner of a blind-end hole, is open in the direction of the end of the coupling member 5 on the side remote from the working head 2. The inner recess 9 accommodates an approximately sleeve-shaped mount 7 which extends coaxially with the longitudinal axis 17 of the attachment brush 5. The mount 7, in turn, forms with its inner contour a blind-end-hole-shaped plug-in opening 24 into which the drive shaft 21 can be accurately plugged. In the implementation shown in FIGS. 2 and 4, both the connecting section of the drive shaft 21 and the plug-in opening 24 of the mount 7 are slightly conically shaped, with the bevel being smaller than 7 degrees to achieve self-locking. The plug-in opening 24 and the drive shaft 21 form in combination a fit for firmly clamping the attachment brush 5 upon the handpiece 4 of the toothbrush 1. In another implementation, the connecting section of the drive shaft 21 and the plug-in opening 24 of the mount 7 are cylindrically shaped.

The drive shaft 21 and the conformably shaped mount 7 can be of an essentially circular configuration when viewed in cross-section. Accordingly, the drive shaft 21 forms an essentially circular cone. As a comparison of FIGS. 2 and 4 shows, the drive shaft 21 and the conformably shaped mount 7 have at their front ends a flattening 15 in the form of two opposite surfaces tapering relative to the longitudinal axis 17.

In one implementation, the whole sleeve-shaped mount 7 in the interior of the coupling member 3 is a two-part configuration. A first mounting member 11 and a second mounting member 12 are both of an approximately half-shell-shaped configuration so that the mount 7 resembles a longitudinally slotted sleeve. The mount 7 can be centrally split in a plane containing the longitudinal axis 17. But, the half-shell-shaped mounting member 11 can also cover an angle segment of less than 180°.

As FIG. 2 shows, the mounting member 11 is formed separately from the coupling member 3, so that it is movable relative to the coupling member 3. By contrast, the second half-shell-shaped mounting member 12 has its end, which is on the side closest to the working head 2, integrally formed on the coupling member 3 at the bottom of the inner recess 9.

Owing to its separate design, the first mounting member 11 is displaceable within the inner recess 9 in axial direction, that is, in the direction of the longitudinal axis 17. With its end close to the working head 2, the mounting member 11 is seated in a bottom recess 25 in the bottom of the inner recess 9. As FIG. 2 shows, at the bottom of the inner recess 9, the mounting member 11 abuts with its front end against a pair of wedge-shaped surfaces 26 formed on the mounting member 11 and/or a bottom contour of the inner recess 9. This pair of wedge-shaped surfaces 26 operates to urge the mounting member 11 radially inwardly on deeper insertion into the inner recess 9, i.e., towards the opposite second mounting member 12, whereby the plug-in opening 24 becomes smaller. For reasons of tolerance, it can be advantageous to provide the two wedge-shaped surfaces with equal angles.

The mounting member 11 has a radially inwardly protruding follower tab 19 against which the drive shaft 21 abuts when it is nearly fully inserted in the plug-in opening 24, so that a further pressing-in motion of the drive shaft 21 entrains the mounting member 11 and urges it deeper axially into the inner recess 9.

In order to firmly clamp the drive shaft 21 within the mount 7, the mounting member 11 can be braced against the drive shaft 21. For this purpose, a lever 6 is provided. In a particular implementation, two approximately half-ring-shaped levers 6 and 60 are provided which combine to form a ring which is seated in the interior of the coupling member 3 and surrounds the mount 7. As FIGS. 2 and 4 show, the ring formed by the two lever segments is seated in the annular gap between the outer contour of the two mounting members 11 and 12 and the inner contour 10 of the coupling member 3 surrounding the mount 7. The toggle joint formed by the two levers 6 and 60 can be arranged closer to the open end of the inner recess 9 rather than at the bottom of the inner recess 9. In the embodiment shown, it sits inside at some distance from the open end of the inner recess 9.

The two half-ring-shaped levers 6 and 60 can be configured as separate ring halves. In another implementation, an integrally formed ring having two lever segments, which are connected to one another by a line of desired bending, enables the two half-ring-shaped segments to be tilted relative to each other. The two levers 6 and 60, or toggle joint segments, can be pivotally connected to one another in the region of the line of desired bending 27, for example, by a tongue-and-groove joint or by an integrally formed bending section.

As FIG. 2 shows, the two levers 6 and 60 have their outer circumference pivotally mounted on the inner contour 10 of the inner recess 9. For this purpose, the inner contour 10 includes a groove-shaped recess extending approximately in the circumferential direction and engaging a holding rib which projects radially on the outer circumference of the levers 6 and 60, cf. FIG. 2. To hold the levers captive, this joint can be mounted in a window in the inner contour by positive engagement.

On its inner circumference, the one lever 6 is equally pivotally connected to the axially movable mounting member 11. Similarly, the outer contour of the mounting member 11 has a groove-shaped recess into which a holding rib engages, projecting radially inwardly on the inner contour of the lever 6. Accordingly, the lever 6 pivots on axial movement of the mounting member 11, thus forming an actuator for the lever 6. Owing to the pivotal joint between the lever 6 and the opposite lever 60, the latter is correspondingly entrained or received, so that both levers 6 and 60 are pivoted by axial movement of the mounting member 11.

This enables the following mode of operation: as the drive shaft 21 is inserted into the mount 7, at the end of the axial plug-in movement, the movable mounting member 11 is entrained or received by the drive shaft 21 through engagement with the follower element 19 and pressed deeper into the inner recess 9. In doing so, the axial movement of the mounting member 11 causes the section of the mounting member 11 at the bottom of the inner recess 9 to more firmly engage the drive shaft 21 by way of the pair of wedge-shaped surfaces 26. Yet, the axial movement of the mounting member 11 actuates the toggle joint mechanism. The two levers 6 and 60 pivot from their initial released position into their clamping position, which, as shown in FIG. 2, can be slightly overstraightened. Although the bracing force is lessened compared to a perfectly straightened position of the levers 6 and 60, the overstraightened position nevertheless ensures a secure locking function. The slightly overstraightened position forces the mounting member 11 into its clamping position within the inner recess 9. When the attachment brush 5 is pulled off the handpiece 4, the toggle joint moves in the reverse direction. As a result of the locking, the axially movable mounting member 11 is first entrained some distance whereby the levers 6 and 60 pivot back. This causes the bracing to release, the locking engagement to release, and enables the drive shaft 21 to withdraw from the mount 7.

FIGS. 5 and 6 show another implementation in which the drive shaft 21 can include, in a mid-section, another flattening 14 forming a constriction on the contour of the drive shaft 21. The two mounting members 11 and 12 are provided with complementary projections fitting closely, snugly or tightly onto the flattening 14 of the drive shaft 21. Because the flattening 14 has the form of a constriction and does not extend beyond the section of the drive shaft 21 engaging the mount 7, but is axially limited, it is not only possible to accomplish a firm clamping function of the drive shaft 21 by frictional engagement as a result of the locking, but also a holding function by positive engagement. Similar to that shown in FIGS. 2 and 3, the drive shaft 21 can be slightly conical as can the inner contour of the mount 7, in order to enable a clamping action that accommodates production tolerances. Advantageously, the bevel 28 is smaller than 7 degrees when it is desired to achieve a self-locking function.

In another implementation shown in FIG. 7, the drive shaft 21 is provided with a projection 14.2, and the mounting members 11, 12 with a corresponding flattening. The projection extends radially about the drive shaft without extending around the entire circumference of the drive shaft. When the attachment brush is pulled off, the projection 14.2 aids in releasing the toggle joint clamping action.

A number of embodiments of the invention have been described. Nevertheless, it will be understood that various modifications may be made without departing from the spirit and scope of the invention. For example, in other implementations, the drive shaft 21 can have a slightly smaller diameter in the clamping region of the levers 6, 60 than in the regions adjacent to the clamping region. When the levers are clamped, the mount 7 is then elastically deformed in the clamping region, thereby enhancing the clamping effect. Accordingly, other embodiments are within the scope of the following claims.

The invention claimed is:

1. An attachment for an electric toothbrush, comprising:
a working head;
a coupling member joined to the working head, and detachably connectable to a toothbrush handpiece by at least one of positive engagement and frictional engagement; and
at least one pivot lever configured to clamp the coupling member upon the toothbrush handpiece;
wherein a lever actuator is provided that is axially movable relative to the coupling member longitudinal direction, the actuator including a follower element that engages the toothbrush handpiece on plugging the attachment onto the toothbrush handpiece, and being operatively associated with the lever by connecting means in such a way that, on plugging on the attachment, the lever actuator becomes displaced axially, thereby moving the lever into its clamping position.

2. The attachment according to claim 1, wherein the coupling member includes a mount into which a connecting member of the toothbrush handpiece is insertable, with the lever being provided for securely clamping the mount against the connecting member.

3. The attachment according to claim 2, wherein the mount is conically shaped.

4. The attachment according to claim 2, wherein the mount forms one of a longitudinally slotted sleeve and a multi-part sleeve.

5. The attachment according to claim 2, wherein the coupling member includes an inner recess into which the connecting member of the toothbrush handpiece is insertable, with the lever being arranged in the inner recess and adapted to be braced between an inner contour of the inner recess and the connecting member of the toothbrush handpiece.

6. The attachment according to claim 2, wherein the coupling member includes a mounting member which is shaped to conform to the connecting member of the toothbrush handpiece, radially and axially movably mounted in relation to a longitudinal axis of the coupling member and is adapted to be moved by the lever onto the connecting member of the toothbrush handpiece.

7. The attachment according to claim 6, wherein the coupling member includes an inner recess into which the connecting member of the toothbrush handpiece is insertable, with the lever being arranged in the inner recess and adapted to be braced between an inner contour of the inner recess and the connecting member of the toothbrush handpiece; and
wherein the mounting member is arranged in the inner recess of the coupling member and spaced from the inner contour of the inner recess, with the lever being arranged between the inner contour of the inner recess and the mounting member.

8. The attachment according to claim 6, wherein the mounting member forms a half-shell-shaped mounting shell having a contour shaped to closely conform to the connecting member of the toothbrush handpiece in coupled condition.

9. The attachment according to claim 8, wherein the mounting member includes at least one flattening.

10. The attachment according to claim 6, wherein the lever actuator is formed by the mounting member, which is shaped to conform to the connecting member of the toothbrush handpiece.

11. The attachment according to claim 10, wherein the connecting means are configured for positive engagement, and/or include a mounting recess and a projection engaging therein.

12. The attachment according to claim 2, wherein the at least one pivot lever includes a pair of opposite levers forming a toggle joint.

13. The attachment according to claim 12, wherein the toggle joint forms one of a slotted ring and a ring split into two pivoted segments into which the connecting member of the toothbrush handpiece is insertable.

14. The attachment according to claim 13, wherein the ring embraces the mount.

15. The attachment according to claim 1, wherein the lever is configured to be self-actuating so that when the attachment is plugged onto the toothbrush handpiece, the lever pivots into its clamping position, and pivots into a released position when the attachment is pulled off the toothbrush handpiece.

16. The attachment according to claim 1, wherein the lever is overstraightened when in its clamping position.

17. The attachment according to claim 1, wherein the coupling member is connectable to the toothbrush handpiece using an axial movement along a longitudinal axis of the coupling member, and the lever is pivotal about a transverse axis transverse to the longitudinal axis.

18. The attachment according to claim 1, wherein the lever is pivotally mounted on a pivot formed with the coupling member.

19. The attachment according to claim 1, wherein the coupling member is shaped to conform to a drive shaft of the toothbrush handpiece, and is adapted to be clamped upon the drive shaft by means of the lever.

20. A toothbrush comprising:
a toothbrush handpiece; and
an attachment comprising:
a working head; a coupling member joined to the working head, and detachably connectable to the toothbrush handpiece; and at least one pivot lever configured to clamp the coupling member upon the toothbrush handpiece; wherein a lever actuator is provided that is axially movable relative to the coupling member longitudinal direction, the actuator including a follower element that engages the toothbrush handpiece on plugging the attachment onto the toothbrush handpiece, and being operatively associated with the lever by connecting means in such a way that, on plugging on the attachment, the lever actuator becomes displaced axially, thereby moving the lever into its clamping position.

21. The toothbrush according to claim 20, wherein the toothbrush handpiece includes one of a cylindrical and a conically tapered drive shaft.

22. The toothbrush according to claim 21, wherein the drive shaft includes one of a flattening and a projection.

23. The toothbrush according to claim 21, wherein the attachment is connectable via the drive shaft.

24. An attachment for an electric toothbrush, comprising:
a working head;
a coupling member joined to the working head, and detachably connectable to a toothbrush handpiece by at least one of positive engagement and frictional engagement; and at least one pivot lever configured to clamp the coupling member upon the toothbrush handpiece; wherein the lever is of a half-ring-shaped configuration.

\* \* \* \* \*